US008680630B2

(12) United States Patent
Bikumandla

(10) Patent No.: US 8,680,630 B2
(45) Date of Patent: Mar. 25, 2014

(54) BACKSIDE STIMULATED SENSOR WITH BACKGROUND CURRENT MANIPULATION

(71) Applicant: Omnivision Technologies, Inc, Santa Clara, CA (US)

(72) Inventor: Manoj Bikumandla, San Jose, CA (US)

(73) Assignee: OmniVision Technologies, Inc., Santa Clara, CA (US)

(*) Notice: Subject to any disclaimer, the term of this patent is extended or adjusted under 35 U.S.C. 154(b) by 0 days.

(21) Appl. No.: 13/950,116

(22) Filed: Jul. 24, 2013

(65) Prior Publication Data

US 2013/0307093 A1 Nov. 21, 2013

Related U.S. Application Data

(63) Continuation of application No. 12/853,160, filed on Aug. 9, 2010, now Pat. No. 8,519,490.

(51) Int. Cl.
*H01L 27/146* (2006.01)
*G01N 27/26* (2006.01)

(52) U.S. Cl.
USPC ....... 257/414; 257/253; 257/446; 204/403.01

(58) Field of Classification Search
USPC ......................... 257/253, 444, 446, 460, 461; 205/787.5, 789
See application file for complete search history.

(56) References Cited

U.S. PATENT DOCUMENTS 5,063,081 A * 11/1991 Cozzette et al. .................. 435/4
5,200,051 A * 4/1993 Cozzette et al. ......... 204/403.07
5,212,050 A * 5/1993 Mier et al. .................... 430/320
5,466,575 A * 11/1995 Cozzette et al. ............. 435/6.11
5,554,339 A * 9/1996 Cozzette et al. ................ 422/50
5,827,415 A * 10/1998 Gur et al. ...................... 204/426
5,837,446 A * 11/1998 Cozzette et al. ............. 435/6.11
5,837,454 A * 11/1998 Cozzette et al. ............. 435/6.11
6,306,594 B1 * 10/2001 Cozzette et al. ............. 435/6.11
6,464,940 B1 * 10/2002 Akioka et al. ............. 422/82.01
7,074,610 B2 * 7/2006 Cozzette et al. ........... 435/287.2
7,105,358 B2 * 9/2006 Majumdar et al. ............ 436/518
7,217,428 B2 * 5/2007 Tuszynski et al. ............ 424/464
7,315,014 B2 * 1/2008 Lee et al. ................... 250/208.1
7,425,749 B2 * 9/2008 Hartzell et al. ............... 257/414
7,432,148 B2 * 10/2008 Li et al. ......................... 438/218
7,595,213 B2 * 9/2009 Kwon et al. .................... 438/60

(Continued)

FOREIGN PATENT DOCUMENTS

CN 1846132 A 12/2009

OTHER PUBLICATIONS

P. Bergveld, "ISFET, Theory and Practice", IEEE Sensor Conference Toronto, Oct. 2003, pp. 1-26.

(Continued)

*Primary Examiner* — Earl Taylor
(74) *Attorney, Agent, or Firm* — Blakely Sokoloff Taylor & Zafman LLP

(57) ABSTRACT

A CMOS (Complementary Metal Oxide Semiconductor) pixel for sensing at least one selected from a biological, chemical, ionic, electrical, mechanical and magnetic stimulus. The CMOS pixel includes a substrate including a backside, a source coupled with the substrate to generate a background current, and a detection element electrically coupled to measure the background current. The stimulus, which is to be provided to the backside, affects a measurable change in the background current.

25 Claims, 15 Drawing Sheets

(56) References Cited

U.S. PATENT DOCUMENTS

| | | | | |
|---|---|---|---|---|
| 7,759,924 | B2 * | 7/2010 | Shekhawat et al. | 324/71.1 |
| 7,794,584 | B2 * | 9/2010 | Chodavarapu et al. | 205/777.5 |
| 7,799,205 | B2 * | 9/2010 | Morgenshtein et al. | 205/789 |
| 7,867,754 | B1 * | 1/2011 | Regnier et al. | 435/287.1 |
| 7,927,789 | B1 * | 4/2011 | Baird et al. | 435/4 |
| 7,968,836 | B2 * | 6/2011 | Cunningham et al. | 250/214.1 |
| 8,026,559 | B2 * | 9/2011 | Chen et al. | 257/414 |
| 8,101,423 | B2 * | 1/2012 | Cunningham et al. | 436/164 |
| 8,129,809 | B2 * | 3/2012 | Jang | 257/436 |
| 8,338,856 | B2 * | 12/2012 | Tai et al. | 257/184 |
| 2002/0090738 | A1 * | 7/2002 | Cozzette et al. | 436/518 |
| 2004/0094784 | A1 * | 5/2004 | Rhodes et al. | 257/291 |
| 2004/0234417 | A1 | 11/2004 | Schienle et al. | |
| 2006/0024813 | A1 * | 2/2006 | Warthoe | 435/287.1 |
| 2006/0030033 | A1 * | 2/2006 | Cunningham et al. | 435/287.2 |
| 2006/0038252 | A1 * | 2/2006 | Mouli | 257/446 |
| 2007/0023851 | A1 * | 2/2007 | Hartzell et al. | 257/414 |
| 2007/0045513 | A1 * | 3/2007 | Lee et al. | 250/208.1 |
| 2007/0048927 | A1 * | 3/2007 | Li et al. | 438/218 |
| 2007/0086001 | A1 * | 4/2007 | Islam et al. | 356/301 |
| 2007/0138028 | A1 * | 6/2007 | Chodavarapu et al. | 205/787.5 |
| 2007/0138583 | A1 * | 6/2007 | Ofek et al. | 257/417 |
| 2007/0141801 | A1 * | 6/2007 | Kwon et al. | 438/400 |
| 2008/0061330 | A1 * | 3/2008 | Shiau et al. | 257/294 |
| 2008/0081769 | A1 * | 4/2008 | Hassibi | 506/9 |
| 2008/0085559 | A1 * | 4/2008 | Hartzell et al. | 436/2 |
| 2008/0268611 | A1 * | 10/2008 | Li et al. | 438/431 |
| 2009/0090937 | A1 * | 4/2009 | Park | 257/252 |
| 2009/0181441 | A1 * | 7/2009 | Jin et al. | 435/180 |
| 2009/0298704 | A1 * | 12/2009 | Anwar et al. | 506/9 |
| 2009/0315137 | A1 * | 12/2009 | Kwon et al. | 257/446 |
| 2010/0009456 | A1 * | 1/2010 | Prins et al. | 436/164 |
| 2010/0038523 | A1 * | 2/2010 | Venezia et al. | 250/216 |
| 2010/0051785 | A1 * | 3/2010 | Dai et al. | 250/208.1 |
| 2010/0052080 | A1 * | 3/2010 | Garcia Tello et al. | 257/414 |
| 2010/0122904 | A1 * | 5/2010 | Hassibi et al. | 204/403.01 |
| 2010/0137143 | A1 * | 6/2010 | Rothberg et al. | 506/2 |
| 2010/0155868 | A1 * | 6/2010 | Jang | 257/432 |
| 2010/0301398 | A1 * | 12/2010 | Rothberg et al. | 257/253 |
| 2011/0127619 | A1 * | 6/2011 | Chen et al. | 257/414 |
| 2011/0199518 | A1 | 8/2011 | Zheng et al. | |
| 2011/0268151 | A1 * | 11/2011 | Hadwen et al. | 374/141 |
| 2012/0006684 | A1 * | 1/2012 | Hadwen et al. | 204/600 |
| 2012/0032235 | A1 * | 2/2012 | Bikumandla | 257/253 |
| 2012/0088682 | A1 * | 4/2012 | Rothberg et al. | 506/9 |
| 2012/0168306 | A1 * | 7/2012 | Hassibi et al. | 204/403.01 |

OTHER PUBLICATIONS

M. Schoning et al., "Recent advances in biologically sensitive field-effect transistors (BioFETs)", Analyst, 2002, 127, pp. 1137-1151.

B. Jang et al., "Biosensor Systems in Standard CMOS Processes: Fact or Fiction?" Proc. of IEEE International Symposium on Industrial Electronics (ISIE), 2008, pp. 2045-2050.

I. Shcherback et al., "Empirical dark current modeling for complementary metal oxide semiconductor active pixel sensor", Opt. Eng. 41 (6), Jun. 2002, pp. 1216-1219.

Kuga, S. et al., "Precise detection of singly mismatched DNA with functionalized diamond electrolyte solution gate FET", 2008 IEEE, pp. 483-486.

* cited by examiner

BACKSIDE STIMULATED SENSOR WITH BACKGROUND CURRENT MANIPULATION

The present application is a continuation of U.S. patent application Ser. No. 12/853,160, filed on Aug. 9, 2010, entitled "BACKSIDE STIMULATED SENSOR WITH BACKGROUND CURRENT MANIPULATION", now U.S. Pat. No. 8,519,490 is hereby incorporated herein by reference.

BACKGROUND

1. Technical Field

Embodiments of affinity based sensors are disclosed herein. In particular, but not exclusively, embodiments of backside stimulated CMOS (Complementary Metal Oxide Semiconductor) type sensors are disclosed herein. In embodiments, the sensors utilize their background current to measure affinity related stimuli to their backside surfaces.

2. Background Information

Affinity based detection is a fundamental method of identification and measurement. For example, affinity based detection may be used to identify and measure the abundance of biological and biochemical analytes. It is an important analytical method in many fields of endeavor including biotechnology. Affinity based biosensors utilize selective interaction and binding of a target analyte with immobilized capturing probes to specifically capture the target analyte onto a solid surface. Such specific capturing generates detectable signals based on the captured analytes. The generated signals correlate with the presence of target analytes, e.g., ions, toxins, polymers, hormones, DNA strands, protein, cells, etc., and hence are used to estimate the analytes' abundance.

To create the target-specific signals, the target analytes in a sample first collide with a capturing layer that is equipped with probes, bind to the probes, and initiate a transduction process, i.e., a process that produces measurable signals, e.g., electrical, mechanical or optical signals, that are produced solely by the captured entities. The signals are then processed by various means, for example, semiconductor based signal processing techniques.

Various affinity based sensors are known in the arts. However, there is a general need in the art for new and useful affinity based sensors.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

Figure 1:
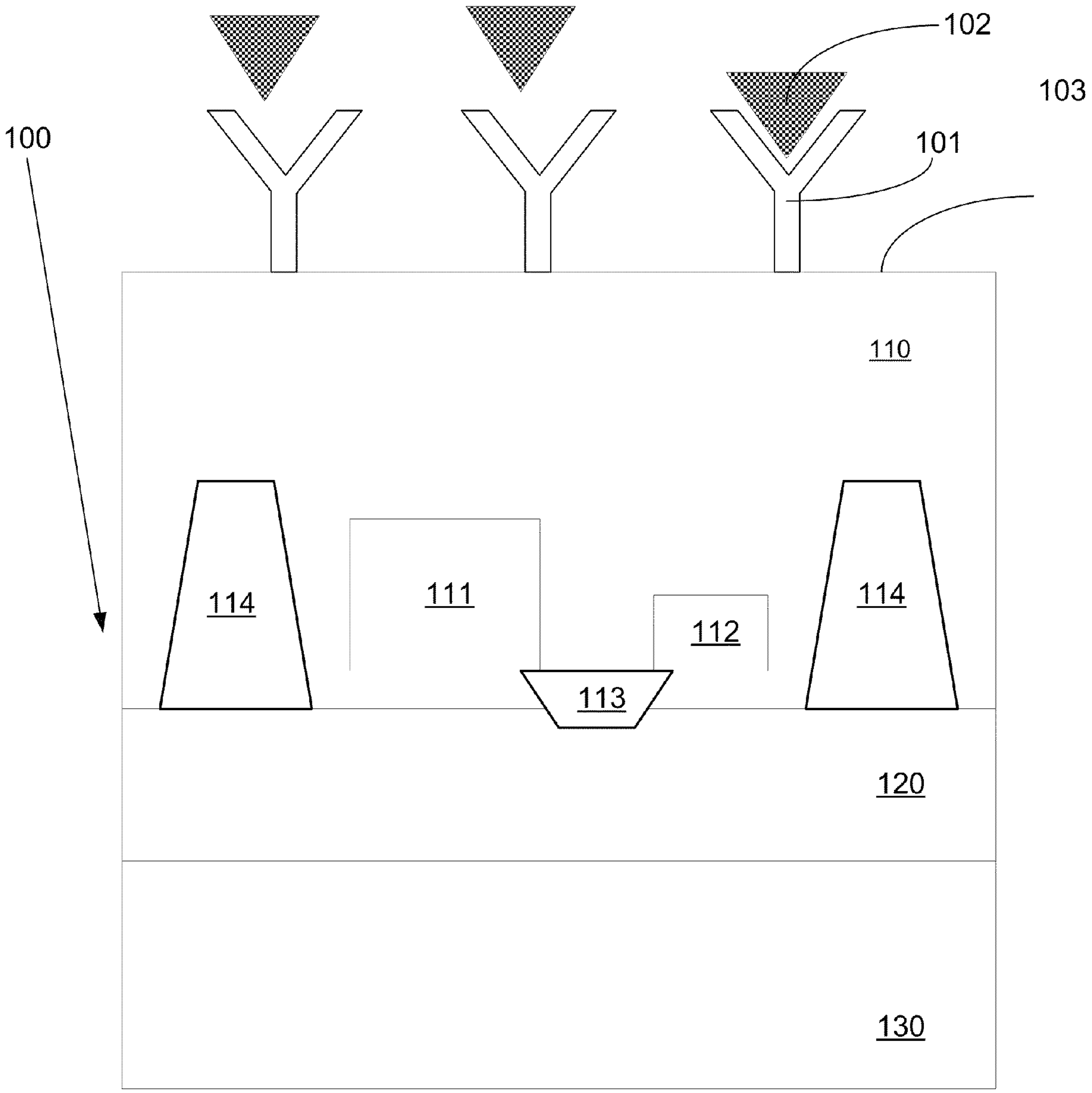
FIG. 1 is a cross sectional view of a CMOS biosensor system showing bio-probes on the backside surface.

In the following description, numerous specific details are set forth. However, it is understood that embodiments of the invention may be practiced without these specific details. In other instances, well-known circuits, structures and techniques have not been shown in detail in order not to obscure the understanding of this description.

Throughout this specification, several terms of art are used. These terms are to take on their ordinary meaning in the art from which they come, unless specifically defined herein or the context of their use would clearly suggest otherwise. "Background Current" is defined herein as the current that flows in a sensor in the absence of an outside signal input such as incident light, and is produced by the inherent characteristics of the material property of the diode and also by stress in the sensor. "Affinity Based Binding" is defined herein as binding of analyte or analytes to probe or probes that are immobilized on a biosensor's detection surface, which produces signals, e.g., optical, magnetic, electrical, electrochemical, or electro-mechanical, that are detectable to the biosensor. "Backside" is defined herein as the side of the substrate that is opposite to the front side, where the metal stack architecture is situated. The terms "biosensor" and "bio-probes" are used to describe the sensor embodiments and the probe embodiments. However, the sensors and probes as described in this disclosure are not limited to bio-applications. The disclosed sensors and probes also pertain to other fields of application, including but not limiting to ionic, chemical, electrical, mechanical and magnetic applications.

In one or more example embodiments, a CMOS pixel, such as a backside stimulated biosensor pixel, for sensing at least one selected from a biological, chemical, ionic, electrical, mechanical and magnetic stimulus, may include a substrate including a backside. A source may be coupled with the substrate to generate a background current. In one aspect, the source to generate the background current may include a diode that is substantially disposed within the substrate. A detection element, such as a circuit, may be electrically coupled to measure the background current. In one or more embodiments, the detection element may be a circuit or other element (e.g., readout circuitry) suitable for reading a pixel of a pixel array. The backside surface of the CMOS pixel may include a layer of probes or bio-probes that affinitively binds to analyte. The affinity based binding increases or decreases electrical charge at or near the backside surface, thereby causing a change in the background current or a stimulus. The stimulus, which is to be provided to the backside, may affect a measurable change in the background current. While the term pixel is used herein, it is not required that the pixel be used for imaging or even that the pixel detect light or electrons corresponding to light. Rather, the pixel may have a photodiode or diode that is used as a source of background current but rather than the photodiode being used as a photodetector the photodiode may optionally be masked (e.g., with a light or electron blocking layer or material), covered, shielded or otherwise blocked from receiving light or corresponding electrons so that it need not actually detect light but may instead be used primarily as a source of background current.

A CMOS "backside" stimulated biosensor pixel is distinguished from a "frontside" stimulated biosensor pixel. A typical CMOS pixel includes a silicon substrate at the bottom, an active device such as a transistor positioned on the substrate, several metal and dielectric layers above the active device. Bio-probes could be positioned on the top surface. The interaction between analytes and bio-probes could produce signals that travel through the metal and dielectric layers to the active device. The signals could then be measured by the active device and supporting circuitry so as to quantify the affinity based effects or the amount of interaction between the analytes and the bio-probes. A significant drawback of a conventional CMOS pixel architecture is the multiple layers of metals and dielectrics that are stacked on top of the active device. These multiple interconnect layers are used to electrically access the transistors, to create a certain circuit topology, and to reduce undesired interaction between a fluidic sample to be analyzed and the semiconductor structures. However, these multiple layers also add to the stack height, would increase the bulk of the biosensor system, and lead to higher system complexity and cost. The thickness of the stack may also cause a reduction in detection sensitivity and accuracy. It is desirable to reduce or eliminate these layers while still allowing access to the transistors and protecting the semiconductor structures from interaction with the fluidic sample.

Instead of transmitting affinity based binding signals into the CMOS integrated circuit from the top of the chip through a top metal layer, the signals may be coupled into the CMOS pixel from the bottom and immediately through the substrate. Instead of being placed on a top metal layer, the bio-probes may be constructed at the backside of the CMOS pixel on the substrate's backside surface. A backside stimulation scheme has been successfully adopted for CMOS image sensor pixels, such as OmniVision™ Backside Illumination CMOS imager products. However, prevalent teaching in the CMOS biosensor art suggests that "electrical signals can only couple from the top and through the pads", i.e., from the front side of the CMOS pixel where the metal/dielectric layers are formed (B. Jang and A. Hassibi, "Biosensor Systems in Standard CMOS Processes: Fact or Fiction?" Proc. of IEEE International Symposium on Industrial Electronics (ISLE), 2049, 2008). A backside stimulation scheme challenges this conventional wisdom.

In addition to backside stimulation, for certain biosensor embodiments, rather than using a conventional electrode to measure electrochemical signals, such as impedance, potential, current and I-V curves, at the analyte-electrode interface, embodiments utilize the CMOS pixel's background current as a measurement tool.

In electronic arts, background current is alternatively known as leakage current. It is primarily caused by electronic devices that are attached to capacitors, such as transistors or diodes, which conduct a small amount of current even when they are turned off. For a CMOS image sensor, background current is frequently referred to as dark current. It is the leakage current at the photodiode node, which discharges the pixel capacitance even though there is no light to stimulate the photodiode. Background current may be described as having at least two components, ideal background current and stress generated background current.

The ideal background current depends in part on the doping concentration, band gap, and the temperature of the photodiode. The ideal background current further includes two sub-components. The first is an injection-diffusion current due to the injection of thermal electrons and holes having a higher energy than the built-in potential energy of the p-n junction. The second is a generation-recombination current due to thermal electron-hole generation or recombination within the p-n junction. These two components depend on applied voltage and temperature. The ideal background current is a result of inherent characteristics of the material properties of the p-n junction.

The stress generated background current is determined by the characteristics of individual defects in the structure of the CMOS pixel. The properties of the material employed in the construction of the CMOS pixel and the supporting devices induce background current in the CMOS pixel through various mechanisms. These mechanisms may include the following. First, the background current may be produced by a junction leakage of the photodiode, as well as other leakages through structural defects or limitations of the photodiode and its surrounding structures. Second, the background current may be produced by a sub-threshold leakage of the transistors that are connected to the photodiode. Third, the background current may be produced by a drain-induced-barrier-lowering leakage, or by a gate-induced drain leakage current of the transistors that are connected to the photodiode.

Of particular significance is the leakage current associated with the depletion region of the photodiode edge and the shallow trench isolation (STI) structure due to the material properties at the interfaces. For example, point defects within the sidewalls of the silicon substrate that adjoin the STI structure may generate surface states that function as leakage paths for electrical charges. Further, dopant ions in general, and boron ions in particular, that are introduced into the STI structure during ion implantation steps, may affect the surface passivation of the silicon substrate that abuts the STI structure. These dopant ions may also generate interface charge states that function as leakage paths for electrical charges.

Background current has been described in an empirical model as $I=\alpha A+\beta n$, where I represents the background current, $\alpha$ represents the coefficient that determines the junction unity area contribution, A represents junction area, $\beta$ represents the coefficient that determines the corner contribution, and n represents the number of corners in the design (Igor Shcherback, Alexander Belenky, and Orly Yadid-Pecht, "Empirical dark current modeling for complementary metal oxide semiconductor active pixel sensor." Opt. Eng. 41(6) 1216-1219, June 2002). The $\alpha A$ term accounts for the ideal background current component, whereas the $\beta n$ term accounts for the stress generated leakage current component.

Background current degrades image quality of a CMOS image sensor. Hence its reduction and elimination is an important goal of CMOS image sensor pixel design. Described herein are various embodiments that utilize the normally undesirable background current as a measurement tool for affinity binding of a biosensor. Rather than aiming to rid the CMOS pixel of the background current, embodiments described herein maintain an appropriate level of background current, and uses it to detect affinity based effects at the surface of a CMOS pixel, such as affinity based binding at a biosensor surface.

For a backside-stimulated CMOS pixel array surface, several sets of circumstances on the backside surface affect the CMOS pixel's background current. In one set of circumstances, the presence of electrical charge on the backside surface affects the background current. In another set of circumstances, mechanical stress on the backside surface affects the background current.

The following experimental results suggest that electrical charge present on the backside surface affects both the background current and the image quality of a CMOS image sensor. In a first experiment, the backside surface contained imperfections of an ionic nature. Accordingly, white spots were present at the sites of imperfection. These white spots had a higher background current value than the surrounding area. After a stripping process step, the surface charge imperfections were removed, thereby eliminating the white spots. Accordingly, the former white spots took on a background current value that was the same as the surrounding area.

In a second experiment, before application of a voltage to a CMOS image sensor array's backside surface, background current was observed for each pixel. Different pixels produced different, but still relatively similar background currents. After a positive voltage application, the surface acquired a positive electrical potential across the board. Accordingly, the background current in different pixels were increased to a point where the entire backside surface became a "white zone". In short, by applying a uniform voltage bias to the backside of a CMOS image sensor, defect-free pixels may be made to look like defective, white spot like pixels, so long as a right voltage level is applied. Conversely, by applying a negative voltage bias, defective pixels may be made to look like defect-free pixels.

These experiments suggest that for a backside-stimulated CMOS pixel, surface charge affects background current behavior. Particularly, positive surface charges increase the background current, whereas negative surface charges decrease the background current. This principle may be used to design new types of CMOS sensors that utilize background current as an indicator to measure affinity based effects at the backside surface. Whereas conventional CMOS sensor systems, such as the biosensors disclosed in U.S. Patent Application Publications 2010/0122904, 2010/0052080, rely on the an active device, such as a diode, to measure input signals of affinity based effects, the background current-based sensor system disclosed in the present application cleverly utilizes the CMOS pixel's innate background current as the basis to measure input signals and affinity based effects. Here, the affinity based effects produce electrical charges at or near the backside surface. These electrical charges modulate the CMOS pixel's background current.

Apart from electrical charges at or near the backside surface, physical stress on the backside surface may also affect background current. As disclosed in U.S. Patent Application 2010/12708330, covering the surface with an extra light shielding layer introduces extra physical stress to the CMOS pixel that alters the background current. This surface stress affect on the CMOS pixel's background current may be employed to enable a CMOS biosensor similar to the one discussed immediately above. Here, instead of producing electrical charges at or near the surface, the affinity based effect produces additional surface stress that in turn affects the CMOS pixel's background current.

Several backside-stimulated CMOS biosensor systems are disclosed. Bio-probes are immobilized on the CMOS's substrate backside surface. The affinity based binding of target analyte and immobilized receptors produce signals that are detected by the CMOS pixel. The CMOS pixel utilizes its innate background current to measure the input signals. One class of embodiments relies on affinity based binding to produce electrical charges at or near the backside surface. An alternate class of embodiments relies on affinity based binding to produce physical stress on the backside surface.

FIG. 1 illustrates a backside stimulated CMOS biosensor pixel 100, in accordance with an embodiment. CMOS biosensor pixel 100 includes metal stack 130, interlayer dielectric 120 disposed over metal stack 130, and substrate layer 110 disposed over interlayer dielectric 120. The metal stack 130 may include one or more levels of interconnects disposed in one or more dielectric or insulating layers. Substrate layer 110 further includes STI structures 114, diode 111, transfer gate 113, and floating diffusion structure 112. The STI structures 114, diode 111, transfer gate 113, and floating diffusion structure 112 are substantially disposed within the substrate 110. On top of or coupled with backside surface 103 are at least one layer of at least one type of immobilized bio-probes 101. During use, as analyte 102 binds to bio-probes 101, the electrical charge characteristic at or near backside surface 103 changes. Such a change of surface characteristic affects the background current behavior of the CMOS biosensor pixel 100. Accordingly, the affinity based binding affects the background current. The change in background current is detected and processed by the CMOS circuitry. It is to be appreciated that another embodiment may include an array of pixels similar to pixel 100.

Figure 2A:
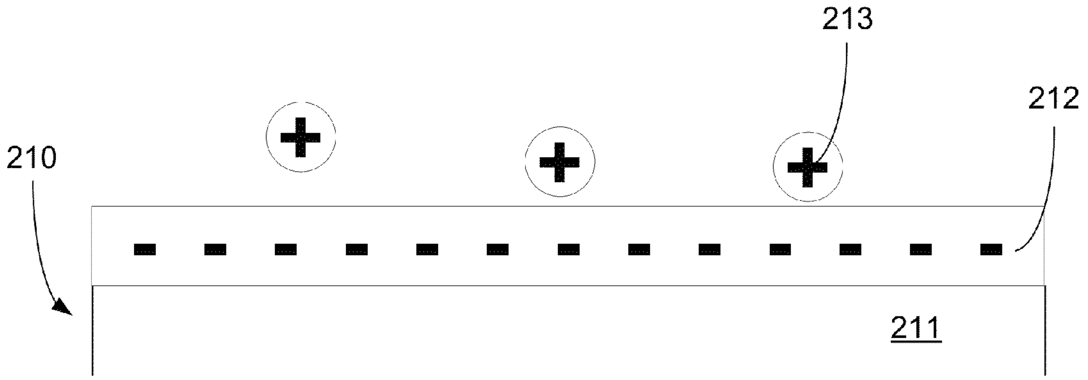
FIG. 2A is a cross sectional view of a CMOS biosensor backside surface showing positive ions binding to the backside surface.

FIGS. 2A through 2H illustrate several embodiments of affinity based binding at or near the backside surface portion of the CMOS biosensor pixel. FIG. 2A shows a positive ion affinity backside surface portion 210 that includes a substrate 211 and a negatively charged surface layer or negatively charged entity 212. The negatively charged surface layer 212 may include $SiO_2$, $Si_3N_4$, $Al_2O_3$, or $Ta_2O_5$ in a proton-acceptor state. The proton-acceptor state of the negatively charged surface layer 212 allows it to bind to positive ion analyte 213 such as proton H+.

Figure 2B:
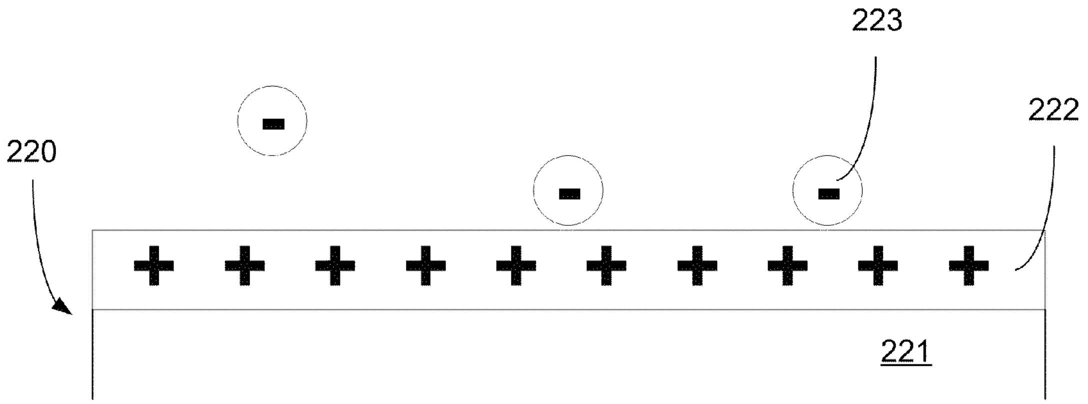
FIG. 2B is a cross sectional view of a CMOS biosensor backside surface showing negative ions binding to the backside surface.

FIG. 2B shows a negative ion affinity backside surface portion 220 that includes a substrate 221 and a positively charged surface layer or positively charged entity 222. The positively charged surface layer 222 may include $SiO_2$, $Si_3N_4$, $Al_2O_3$, or $Ta_2O_5$ in a hydroxide-acceptor state. The hydroxide-acceptor state of the positively charged surface layer 222 allows it to bind to negative ion analyte 223, such as hydroxide OH−.

Figure 2C:
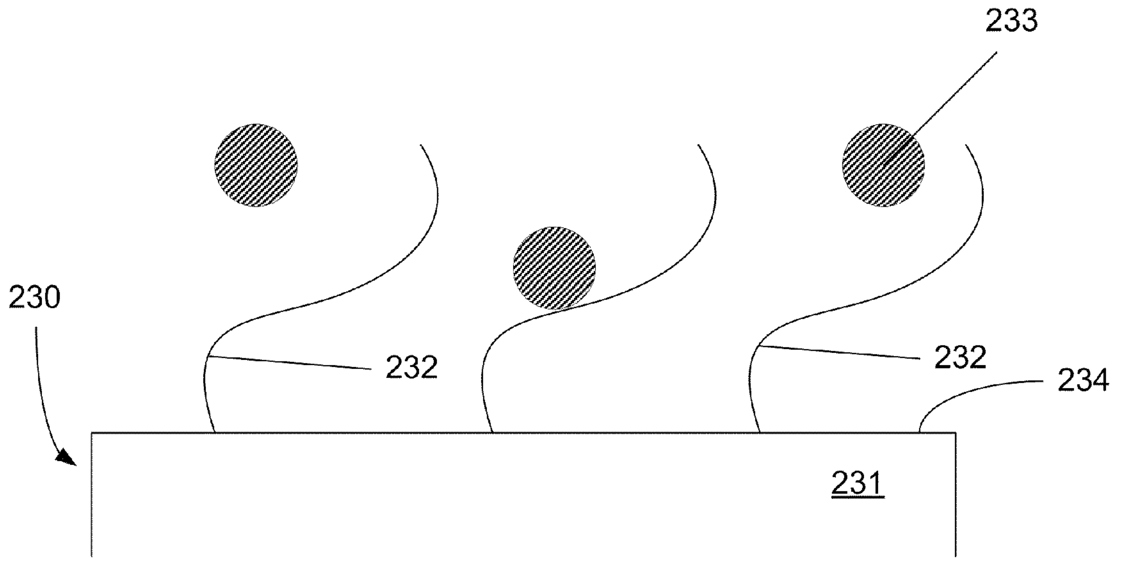
FIG. 2C is a cross sectional view of a CMOS biosensor backside surface showing heparin molecules binding to protamine bio-receptors on the backside surface.

FIG. 2C shows a heparin affinity backside surface portion 230 that includes substrate 231 and protamine probes 232 that are attached to the substrate surface 234. Protamine is a positively charged protein that affinitively binds to negatively charged heparin 233, which is an anticoagulant, i.e., a blood thinner, that is widely used in medical procedures such as renal dialysis, open heart bypass surgery, and treatment of blood clots. Heparin level should be well controlled because heparin overdose leads to dangerous bleeding complications. Affinity based binding between protamine probes 232 and heparin 233 may change the electric charge characteristics at or near the heparin affinity backside surface portion 230, which is part of the CMOS biosensor pixel 100 shown in FIG. 1. Such a change affects background current of the CMOS biosensor pixel 100. In an alternative embodiment, heparin may be used as a bio-probe to detect protamine analyte. In such an embodiment, the CMOS biosensor system functions as a protamine sensor. Alternatively other positively and negatively charged proteins, or other complementary protein pairs entirely may be used.

Figure 2D:
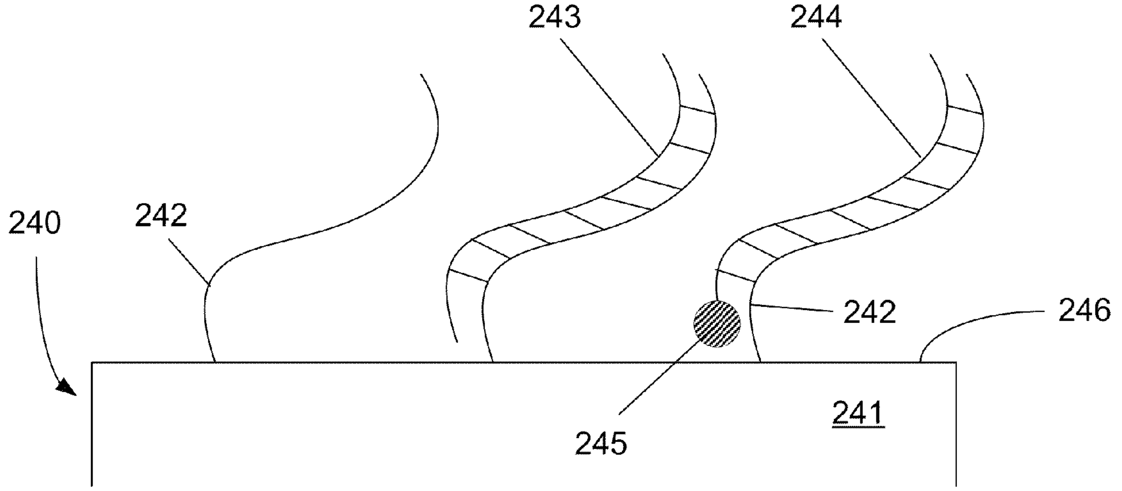
FIG. 2D is a cross sectional view of a CMOS biosensor backside surface showing target DNA binding to probe DNA bio-probes on the backside surface.

FIG. 2D shows a DNA affinity backside surface portion 240 that includes substrate 241 and DNA probes 242 that are attached to the substrate surface 246. DNA probes 242 are single strand DNA molecules that complementarily bind to analyte, i.e., target DNA 243. As target DNA 243 binds to DNA probes 242, the electric charge characteristics of DNA affinity backside surface portion 240 changes. Such change affects the background current of the CMOS biosensor pixel 100 shown in FIG. 1. To increase detection sensitivity, target DNA may be modified to produce tagged target DNA 244 by attaching label 245 to the target DNA. Label 245 amplifies the effect of affinity based binding on the electrical characteristics of the CMOS biosensor pixel 100 shown in FIG. 1. For example, label 245 may be an electric charge that increases the presence of electric charge at or near the DNA affinity surface 240. Label 245 may also be magnetic in nature, and affects surface characteristics through electromagnetic effects. Label 245 may also be a redox label such as ferrocene, that may either donate or accept electrons.

Figure 2E:
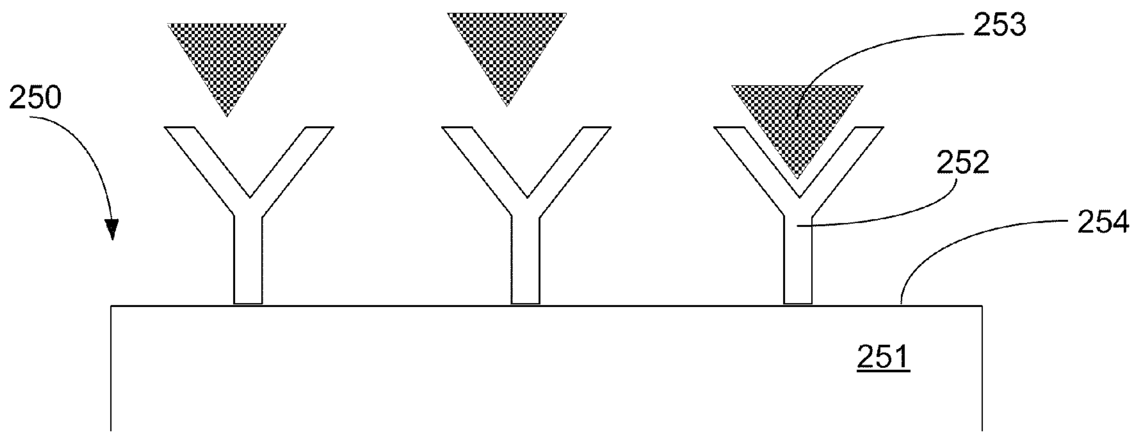
FIG. 2E is a cross sectional view of a CMOS biosensor backside surface showing target antigen binding to antigen bio-probes on the backside surface.

FIG. 2E shows an antibody-antigen affinity backside surface portion 250 that includes substrate 251 and antibody probes 452 that are attached to the substrate surface 254. As analyte antibody 253 affinitively binds to antibody probes 252, the affinity based binding changes the electric charge characteristics of the antibody-antigen affinity surface 250. In the present embodiment, antibodies are used as bio-probes and antigens are used as analyte. For example, the analyte may be an antigen toxin produced by an anthrax bacterium, and the bio-probe may be an antibody that specifically binds to the anthrax antigen. Alternatively, if analyte is an antibody, e.g., the HIV antibody in an HIV diagnostic test, then an HIV-specific antigen may be used as a bio-probe that is attached to the antibody-antigen affinity surface 250. Similar to the DNA-related embodiment, the antigen and antibody in these antigen-antibody embodiments may be tagged with labels in order to increase detection sensitivity.

Figure 2F:
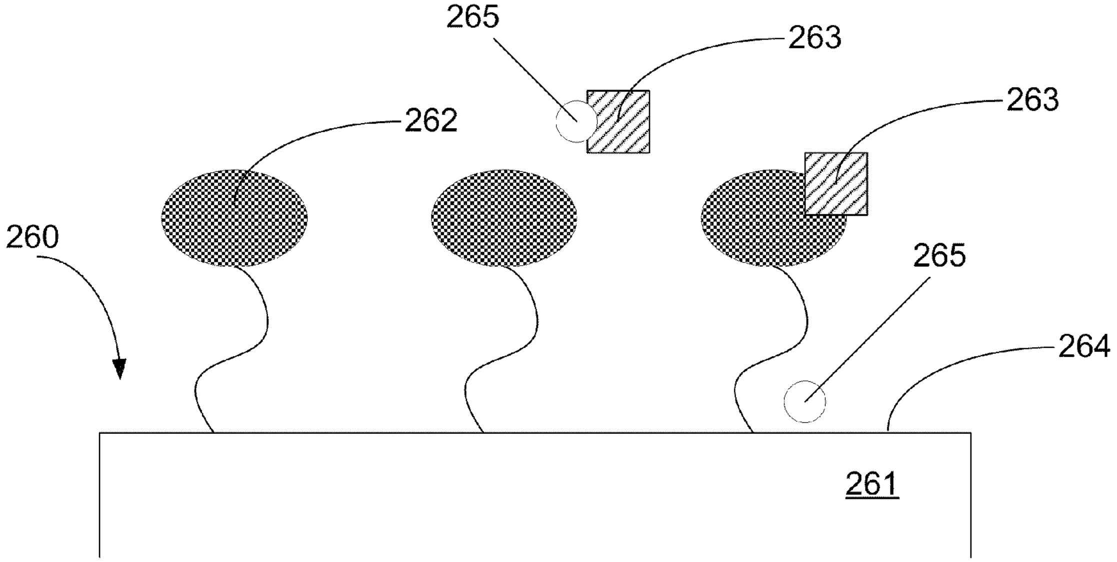
FIG. 2F is a cross sectional view of a CMOS biosensor backside surface showing analyte binding to enzyme bio-probes on the backside surface.

FIG. 2F shows an enzyme affinity backside surface portion 260 that includes substrate 261 and enzyme probes 262 that are attached to the substrate surface 264. By way of example, the enzyme probe may be a penicillinase that converts penicillin into penicilloic acid, a urease that converts urea into $CO_2$ and ammonium, or a glucose oxidase that converts glucose into gluconic acid. Examples of the analyte may be penicillin, urea, or glucose. As analyte 263 binds to enzyme probes 262, the affinity based binding results in an enzymatic reaction that changes the electric charge characteristics of the enzyme affinity backside surface portion 260. For example, the enzymatic reaction may produce a reaction product 265 that affects the surface characteristics of the enzyme affinity surface 260. Examples of the reaction product may be penicilloic acid, $CO_2$ and ammonium, or gluconic acid.

Figure 2G:
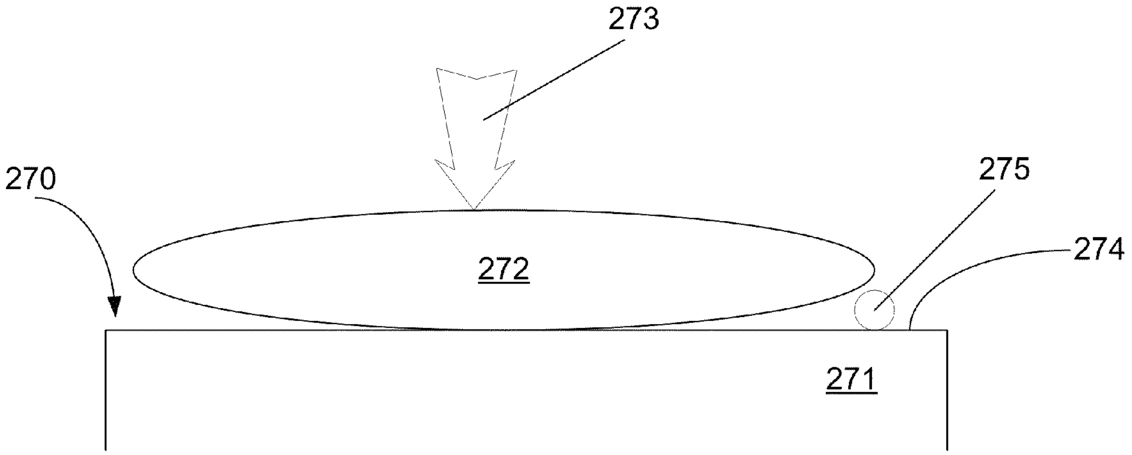
FIG. 2G is a cross sectional view of a CMOS biosensor backside surface showing analyte stimulating a cellular bio-probe on the backside surface.

FIG. 2G shows a cell affinity backside surface portion 270 that includes substrate 271 and a cell probe 272 that is attached to the substrate surface 274. The cell probe 272 may substantially cover the backside surface of a CMOS biosensor pixel 100 as shown in FIG. 1. As analyte stimulus 273 impacts the cell probe 272, the resulting reaction changes the electric charge characteristics of the cell affinity backside surface portion 270. For example, the reaction may produce a reaction product 275 that affects the surface characteristics of the enzyme affinity backside surface portion 270. Alternatively, the cell probe 272 may be a cardiac cell, a muscular cell, or a neuronal cell that produces electrical impulses at or near the substrate surface 274.

Figure 2H:
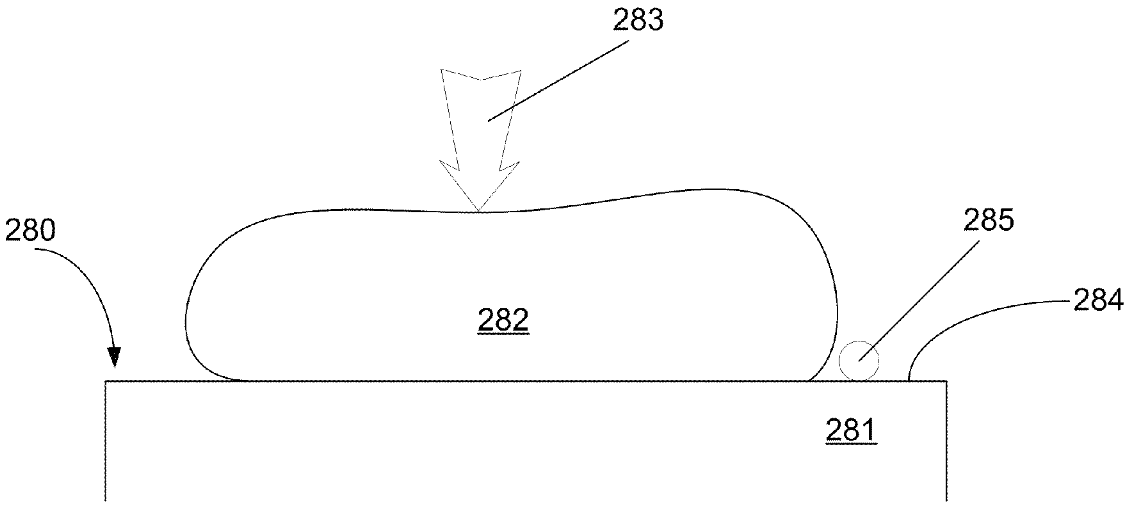
FIG. 2H is a cross sectional view of a CMOS biosensor backside surface showing analyte stimulating a tissue bio-probe on the backside surface.

FIG. 2H shows a tissue affinity backside surface portion 280 that includes substrate 281 and tissue probe 282 that are attached to the substrate surface 284. The tissue probe 282 may substantially cover the backside surface of one or several CMOS biosensor pixels. As analyte stimulus 283 impacts tissue probe 282, the resulting reaction changes the electric charge characteristics of the tissue affinity backside surface portion 280. For example, the reaction may produce a reaction product 285 that affects surface characteristics of the tissue affinity backside surface portion 280. Alternatively, the tissue probe 282 may be an insect antenna that senses analyte stimulus 283 in the environment. The sensing of analyte stimulus 283 produces electrical impulses at or near the substrate surface 284.

FIGS. 3A through 3E illustrate several embodiments of manipulating a CMOS pixel's background current so that it may be utilized to measure the CMOS pixel's surface characteristics. By way of example, the background current may have a range of 10 to 100 electrons per second. In one embodiment, the background current may be approximately 50 electrons per second. An appropriate background current level allows a backside surface stimulus to produce a relatively high signal to noise ratio, which is desirable for detection sensitivity.

In one set of circumstances, the geometry of a diode in the CMOS pixel is manipulated or different than typical (e.g., not cubic) to generate a desirable level of background current. In another set of circumstances, the STI structure is manipulated or different than typical (e.g., rougher or different doping than adjacent areas) to generate a desirable level of background current. Yet in another set of circumstances, the background current is dynamically controlled.

Figure 3A:
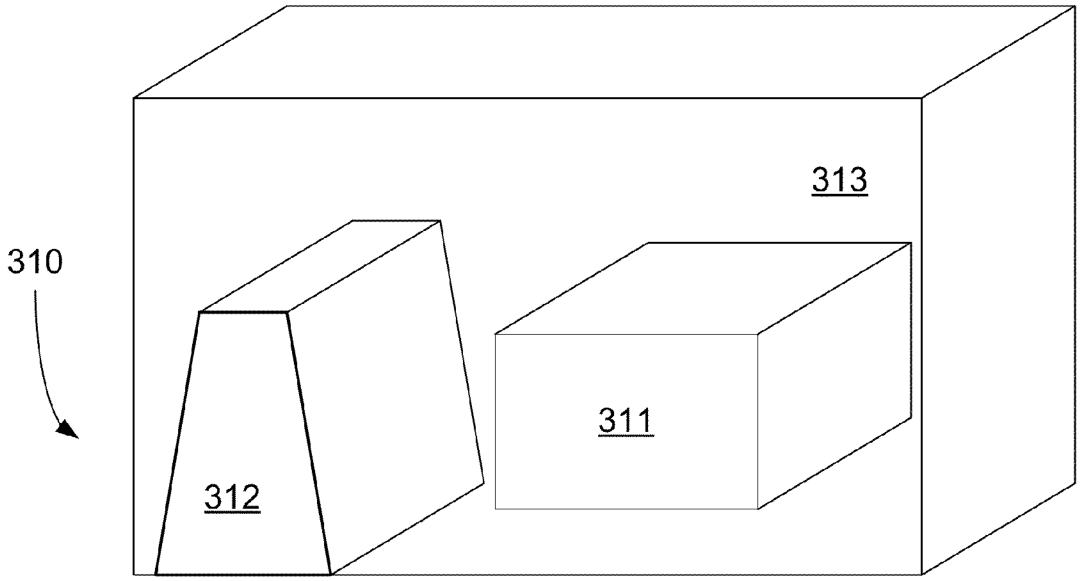
FIG. 3A is a perspective sectional view of a CMOS pixel that contains a diode and STI structure, without manipulation to the diode or the STI structure.

FIG. 3A is a perspective view that shows a CMOS pixel 310 that contains substrate 313, a diode 311 and an STI structure 312 inside the CMOS pixel 310. Neither the diode 311 nor the STI structure 312 has been manipulated. The geometry of the diode 311 is cuboid (e.g., cubic or rectangular solid). That is the planar cross section is rectangular or square.

Figure 3B:
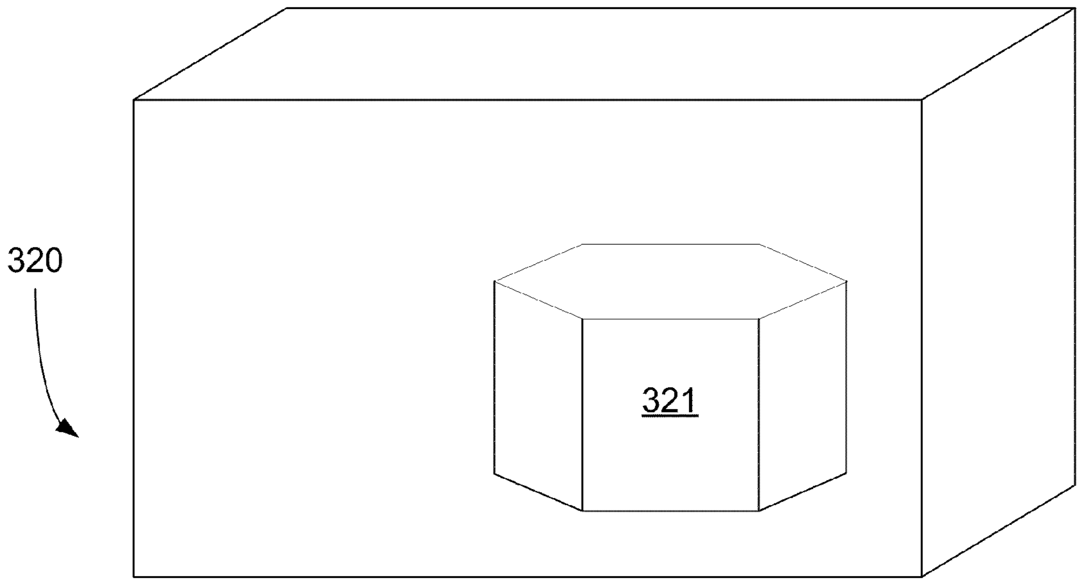
FIG. 3B is a perspective sectional view of a CMOS pixel that contains a diode that has been manipulated to possess a different geometric shape from an unmanipulated diode.

FIG. 3B is a perspective view that shows a CMOS pixel 320 that contains a manipulated diode 321. By way of example, the manipulated diode has a cross sectional geometry that resembles a hexagon. The overall shape is hexagonal solid. This geometry is different from the unmanipulated cuboid diode 311 as shown in FIG. 3A, whose cross sectional geometry resembles a rectangle or square. A hexagon shaped diode may produce a background current that is different from the background current produced by a cuboid diode. Several factors may cause the hexagon shaped diode to produce a different background current from the rectangular diode. An example of such factors may be that the hexagon shaped diode has more corners and/or angles. Other shapes besides hexagonal are possible, such as having cross sectional shapes with more than four sides. In one or more embodiments, a diode may have more vertical sides or more corners than a cubic or rectangular solid. In one or more embodiments, a diode 321 may have either more angles than a cuboid or less angles than a cuboid.

In one or more embodiments, the source to generate the background current may include a shallow trench isolation (STI) structure that is substantially disposed within the substrate. In one or more embodiments, the STI structure of the CMOS biosensor pixel is manipulated or different than typical (e.g., rougher than a typical STI structure or lighter doping profile around it) for the same purpose.

Figure 3C:
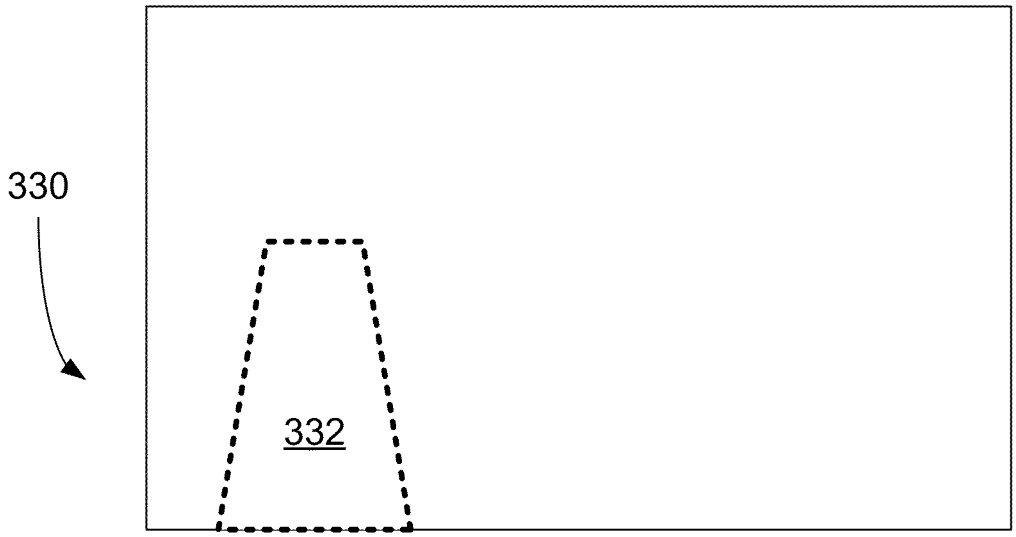
FIG. 3C is a cross sectional view of a CMOS pixel that contains an STI structure that has been manipulated to possess a surface that is rougher than that of an unmanipulated STI structure.

FIG. 3C is a cross sectional view that shows a CMOS pixel 330 that contains a manipulated STI structure 332. By way of example, the manipulated STI structure 332 contains one or more edges that are rougher than an unmanipulated STI structure. The relative roughness of the edges causes a different amount of stress from smooth edges, resulting in a different level of background current.

Figure 3D:
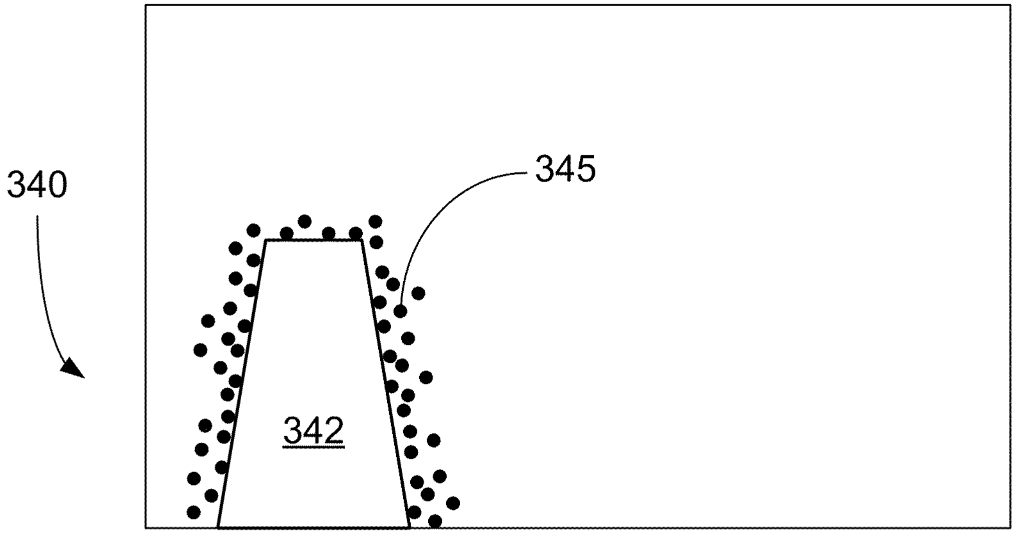
FIG. 3D is a cross sectional view of a CMOS pixel that has been manipulated to contain dopant that affects the background current of the CMOS pixel.

FIG. 3D is a cross sectional view that shows a CMOS pixel 340 that contains dopant 345. By way of example, dopant 345 may include boron ions. Dopant 345 may be around the STI structure 342. Dopant 345 may have a higher concentration range, or a lower concentration range compared to regions farther away from the STI. An example of the dopant concentration range may be approximately 1014 to 1016 ions per cm3. Another example of the dopant concentration range may be approximately 1017 to 1020 ions per cm3. The presence of dopant 345 that is substantially within a predetermined concentration range affects the surface passivation of the part of substrate 343 that abut the STI structure 342, and generates interface charge states that function as leakage paths for electrical charges, thereby affecting background current of the CMOS pixel 340.

Figure 3E:
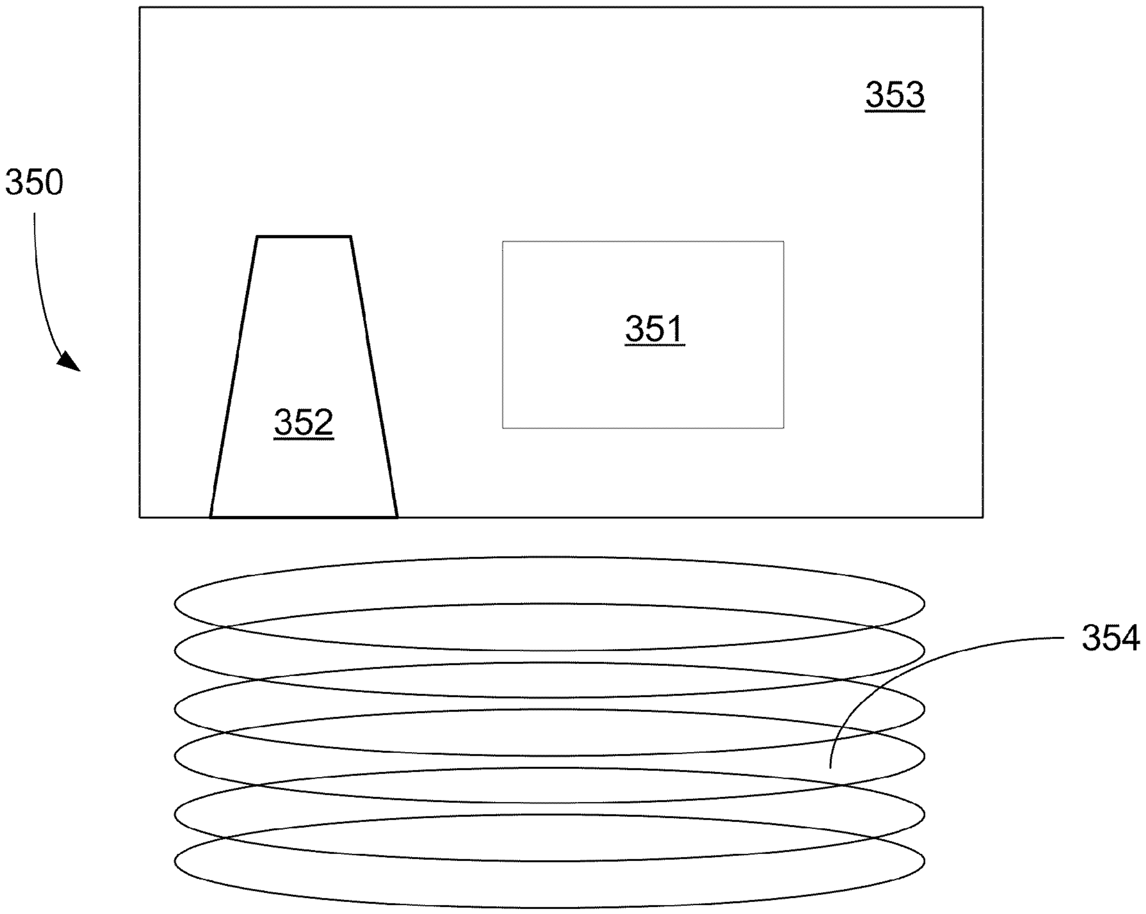
FIG. 3E is a cross sectional view of a CMOS pixel in the vicinity of an inductive element or member that alters the temperature of the CMOS pixel, thereby affecting the background current of the CMOS pixel.

FIG. 3E is a cross sectional view that shows a CMOS pixel 350 that contains substrate 353, a diode 351 and an STI structure 352. An inductive coil 354 or other heater or heating element such as a resistive heater is positioned in the vicinity of or proximate the CMOS pixel 350, for example coupled with the substrate 353. The inductive coil 354 may be manipulated in order to affect the temperature of the CMOS pixel 350. As used herein the inductive coil is in the vicinity of or proximate the CMOS pixel if it is located sufficiently to affect the temperature of the CMOS pixel. By way of example, an electric current may be passed through the inductive coil 354 to heat it. The inductive coil 354 may serve as a temperature reference. The heating of the inductive coil 354 may affect the temperature of the CMOS pixel 350. A change of temperature in the CMOS pixel 350 affects its background current.

Figure 3F:
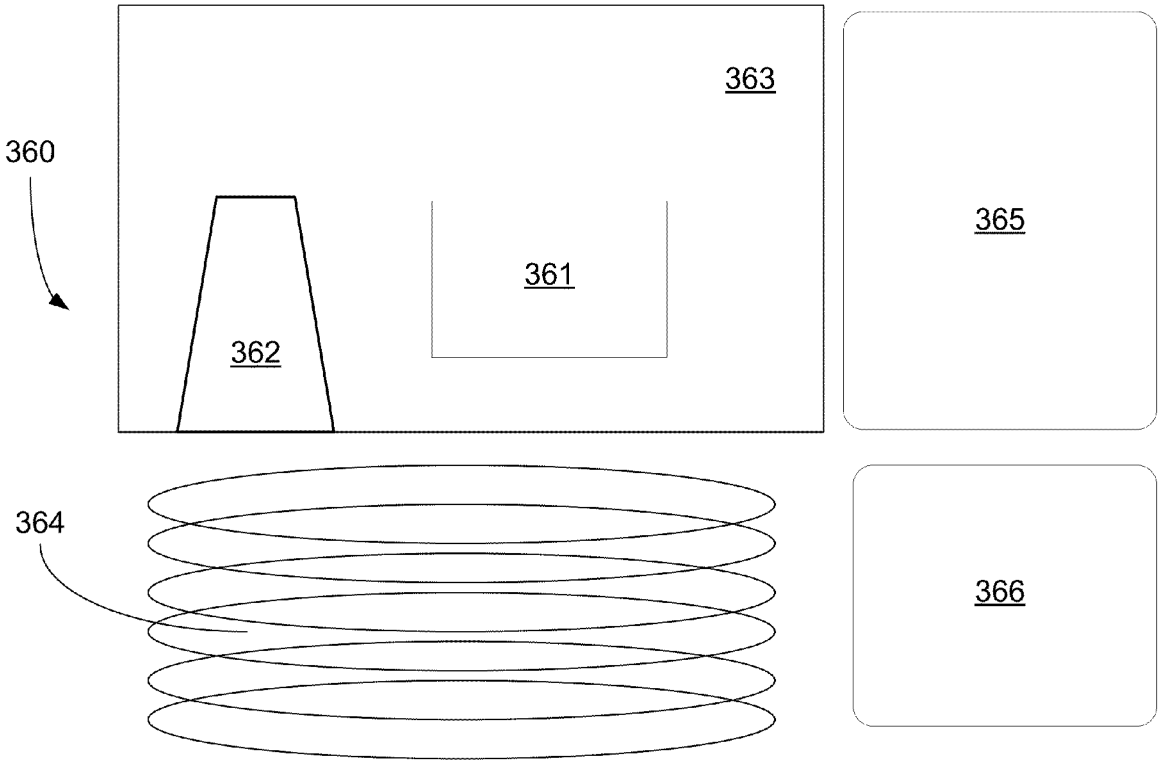
FIG. 3F is a cross sectional view of a CMOS pixel in the vicinity of a inductive element or member, a temperature sensor, and a reference pixel, forming a feedback mechanism that controls the temperature of the CMOS pixel, thereby affecting the background current of the CMOS pixel.

FIG. 3F is a cross sectional view that shows an inductive coil 364 that is positioned in the vicinity of a CMOS pixel 360. A temperature sensor 366 is coupled to both a reference pixel 365 and the inductive coil 364 so that the inductive coil 364 controls the temperature of the CMOS pixel 360 relative to the reference pixel 365. The reference pixel, the temperature sensor, and the inductive member may form a feedback mechanism to control a temperature of the CMOS pixel.

Figure 4A:
FIG. 4A is a cross sectional view of a CMOS pixel array that detects the movement of charged entities at or near the backside surface.

FIG. 4A is a cross sectional view that shows a CMOS pixel array 400 that includes a multitude of CMOS pixels 402, 403 and 404. The CMOS pixel array 400 includes a backside surface layer 401 that may sense the presence of electrical charges. Since each individual CMOS pixel can detect electrical charge or charges above it, the array of CMOS pixels may detect the movement of electrical charge or charges. Movement detection of charged entities may be used to measure the properties of these charged entities such as their mass, size, shape, or orientation.

In one or more embodiments, a biosensor system may include a backside of a substrate, an array of CMOS pixels underneath the backside of the substrate, and a multitude of bump structures coupled with the backside of the substrate. As used herein, a multitude includes at least 20, in some cases at least 50, in some cases at least 100, or more. The multitude of bump structures may be substantially separated by voids.

Figure 4B:
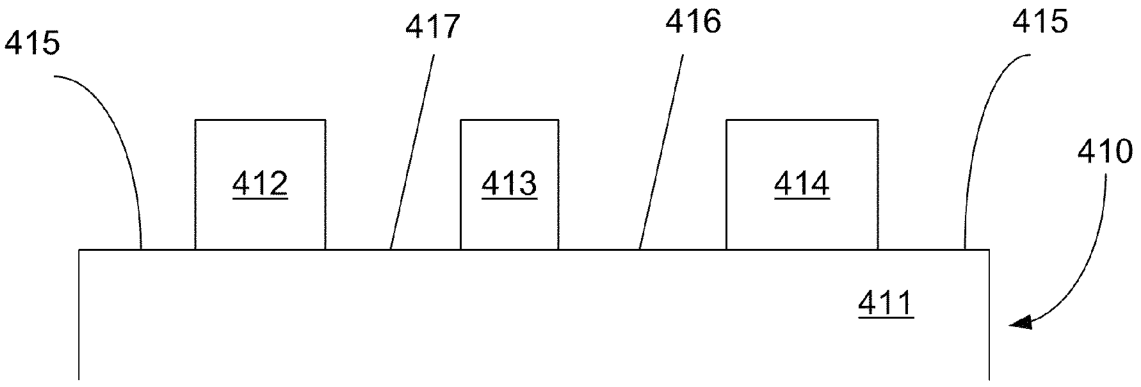
FIG. 4B is a cross sectional view of a modified backside surface of a CMOS pixel array where bump structures form channels that facilitates the detection of the movement of charged entities.

FIG. 4B is a cross sectional view that shows a modified backside surface portion 410 of the CMOS pixel array 400 as disclosed in FIG. 4A. The modified backside surface layer 410 includes a substrate 411, and bump structures 412, 413 and 414 that are situated on surface 415. The bump structures 412, 413 and 414 may form cavities 416 and 417 between them. The bump structures and the cavities may assist the measurement of the flow of particles, electrical charges and other entities on the surface 415. By way of example, the bump structures and the cavities may be arranged to form channels that may direct the flow of particles, electrical charges and other entities. In another example, the cavities may be of different sizes, thereby allowing the separation and sorting of particles, electrical charges and other entities.

In another set of embodiments, a cantilever structure is constructed on top of the backside surface of a CMOS biosensor pixel. Bio-probes are attached to the cantilever structure. Affinity based binding between analyte and the bio-probes affect the stress condition of the CMOS pixel's backside surface, thereby causing a change in the background current.

Figure 5:
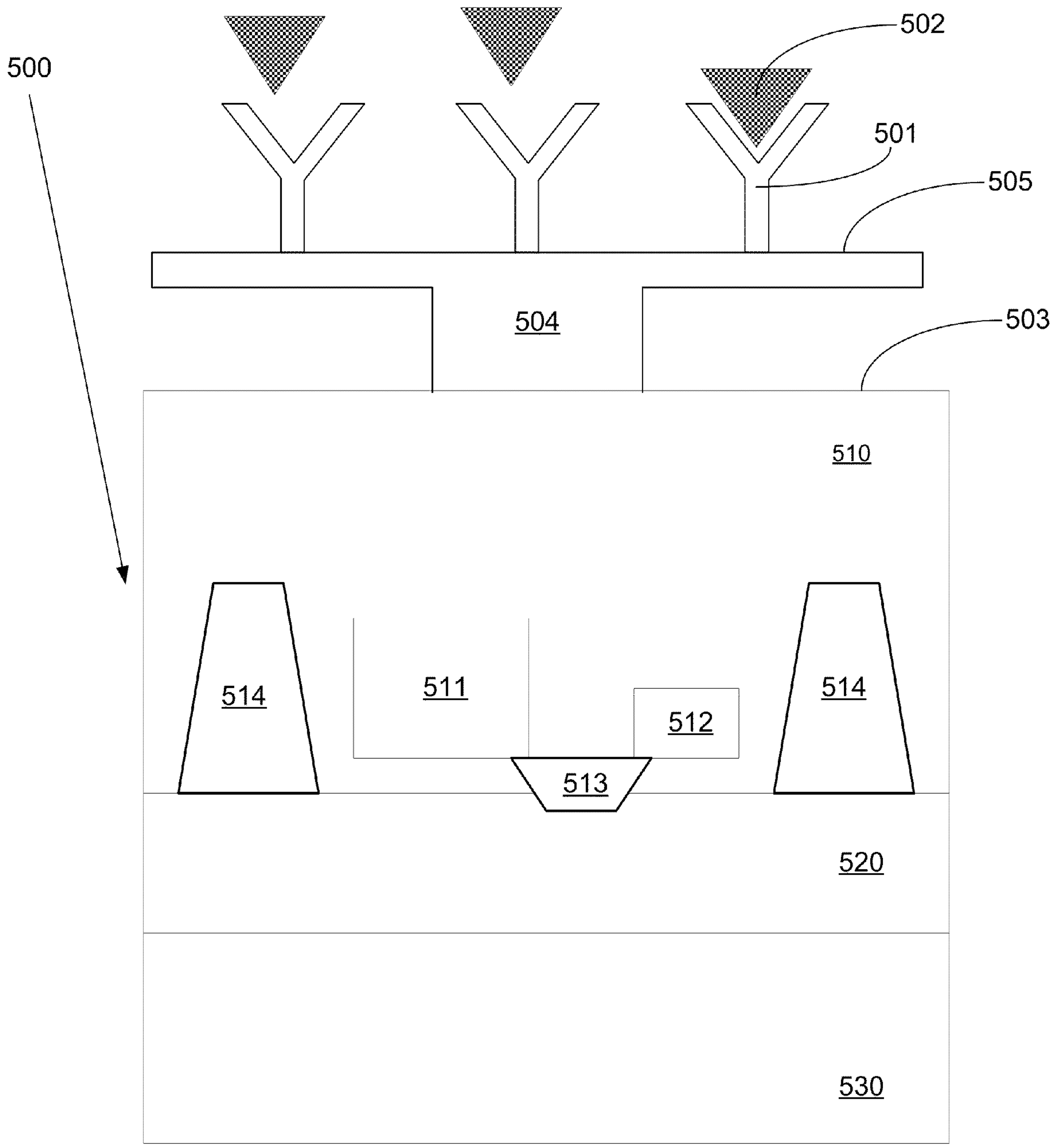
FIG. 5 is a cross sectional view of a CMOS biosensor system that contains a cantilever structure on its backside surface.

FIG. 5 illustrates a backside stimulated CMOS biosensor pixel 500, in accordance with an embodiment. Aside from differences specifically mentioned, the pixel 500 may be similar to and/or have features of the pixel 100 of FIG. 1. For brevity, these features will not be unnecessarily repeated. CMOS biosensor pixel 500 includes metal stack 530, inter-layer dielectric 520, and substrate layer 510. Substrate layer 510 further includes STI structures 514, diode 511, transfer gate 513, and floating diffusion member 512. On top of the CMOS backside surface 503 is a cantilever 504. In one embodiment, the cantilever 504 is substantially situated on or coupled with the CMOS backside surface 503. Cantilever 504 includes a detection surface 505, onto which bio-probes 501 are immobilized or coupled. Analyte 502 may bind to bio-probes 501, thereby adding mass to the cantilever 504.

Accordingly, the stress on the CMOS backside surface 503 changes. Such change of surface stress affects the background current behavior of the CMOS biosensor pixel 500. The changes in the background current is detected and processed by the CMOS circuitry.

Cantilever 504 may have different modes of operation. By way of example, cantilever 504 may have a static mode of operation. In the static mode, affinity based binding of analyte 502 to bio-probes 501 causes a static bending of the cantilever 504. The static bending changes the surface stress of the CMOS backside surface 503, thereby causing a detectable change in the background current of the CMOS biosensor pixel 500.

In another example, cantilever 504 may have a dynamic mode of operation. In the dynamic mode, cantilever 504 may be mechanically excited substantially at its resonant frequency. The mechanical excitation may be produced by various forces. By way of example, one mechanical excitation force may be a piezoelectric force. The mechanical excitation of cantilever 504 may cause dynamic stress cycles on the CMOS backside surface 503. Affinity based binding of analyte 502 to bio-probes 501 may add additional mass to the cantilever 504, causing a shift in the resonant frequency. The shift of resonant frequency may cause a corresponding frequency shift of dynamic stress cycles on the CMOS backside surface 503, which is detectable by monitoring the background current of the CMOS biosensor pixel 500. An alternate embodiment may include an array of cantilevers with each cantilever corresponding to a pixel in a corresponding array of pixels.

Figure 6A:
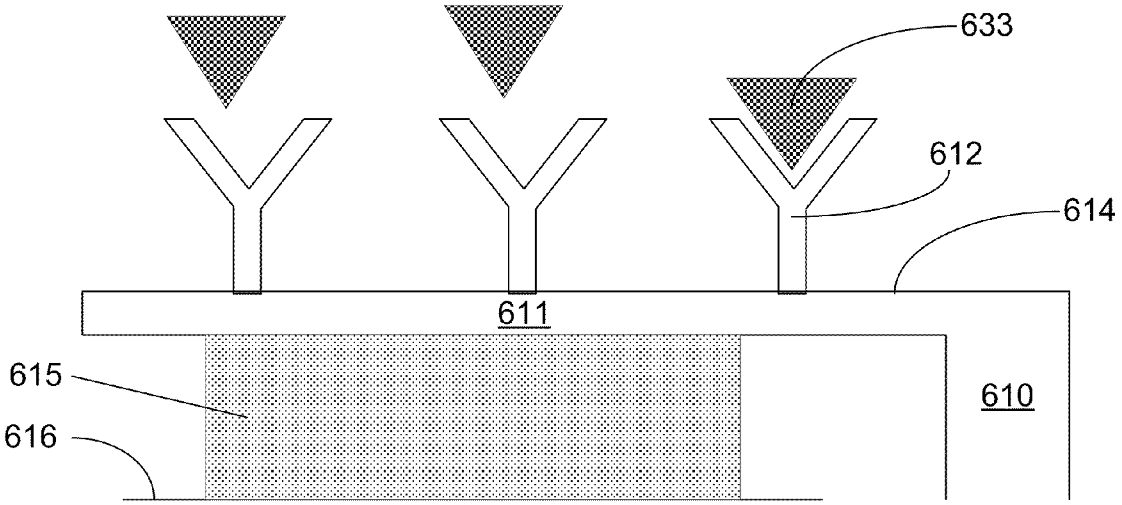
FIG. 6A is a cross sectional view of the backside surface a CMOS biosensor pixel that includes a cantilever structure that couples to the backside surface through a block type structure.
Figure 6B:
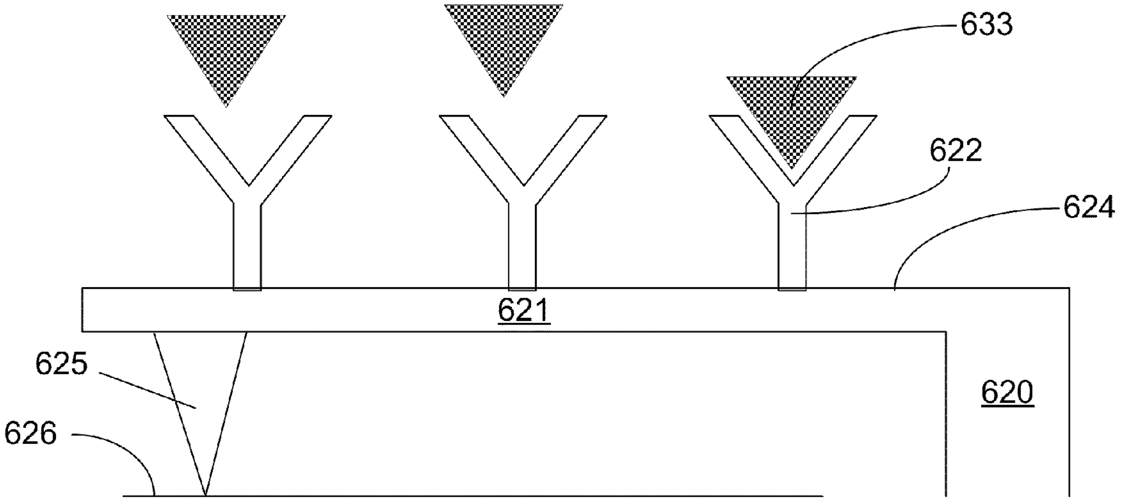
FIG. 6B is a cross sectional view of the backside surface a CMOS biosensor pixel that includes a cantilever structure that couples to the backside surface through a tip type structure.
Figure 6C:
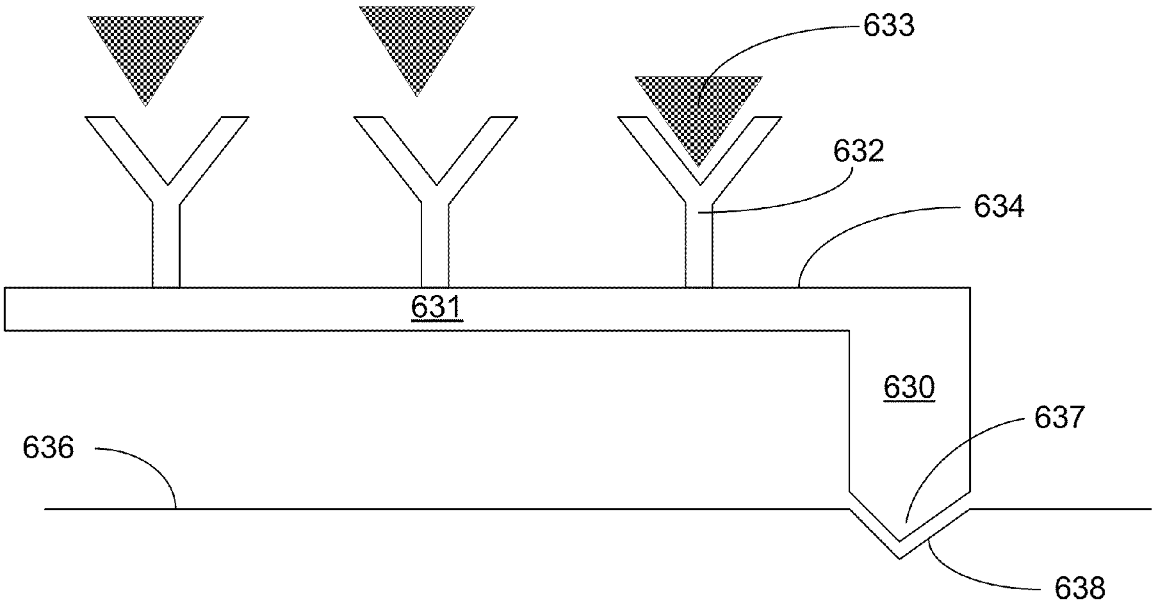
FIG. 6C is a cross sectional view of the backside surface a CMOS biosensor pixel that includes a cantilever structure that is substantially situated on the backside surface.

FIGS. 6A through 6C illustrate several embodiments of coupling between the cantilever and the CMOS backside surface in additional to FIG. 5. FIG. 6A shows a cantilever 610 having a cantilever arm 611. Bio-probes 612 are attached to a cantilever arm surface 614. The cantilever arm 611 is substantially coupled to a CMOS backside surface 616 through an intermediate member 615. By way of example, as analyte 633 may bind to bio-probes 612, the cantilever arm 611 bends. The resulting stress may be transferred to the CMOS backside surface 616 through the intermediate member 615. The intermediate member 615 may be various convenient materials. In another example, the cantilever arm 611 may be mechanically excited, resulting in cyclic motion of the cantilever arm 611. The resulting stress cycles may be transferred to the CMOS backside surface 616 through the intermediate member 615.

FIG. 6B shows a cantilever 620 having a cantilever arm 612. Bio-probes 622 are attached to a cantilever arm surface 624. The bio-probes 622 may be affinitively bound to analyte 623. The cantilever arm 621 may be coupled to a CMOS backside surface 626 through a tip member 625. The tip member 625 may transfer stress and motion of the cantilever arm 621 to the CMOS backside surface 626. Similar to the embodiment disclosed in the previous paragraph, the present embodiment may have several modes of operation, including a static mode and a dynamic mode.

FIG. 6C shows a cantilever 630 having a cantilever arm 632. The cantilever 630 includes a base portion 637. The cantilever 630 may be substantially situated on a CMOS backside surface 636, with the base portion 637 substantially situated onto a notch-like structure 638 that is within the CMOS backside surface 636. The interaction between the base portion 637 and the notch-like structure 638 may facilitate the transfer of stress between the cantilever 630 and the CMOS backside surface 636. Bio-probes 632 may be attached to a cantilever arm surface 634. The bio-probes 632 may be affinitively bound to analyte 633. The affinity based binding adds to the mass of the cantilever 630. In a static mode of operation, the added mass affects the stress on the CMOS backside surface 636. In a dynamic mode of operation, the added mass affects the frequency of cyclic stress of the CMOS backside surface 636.

Figure 7:
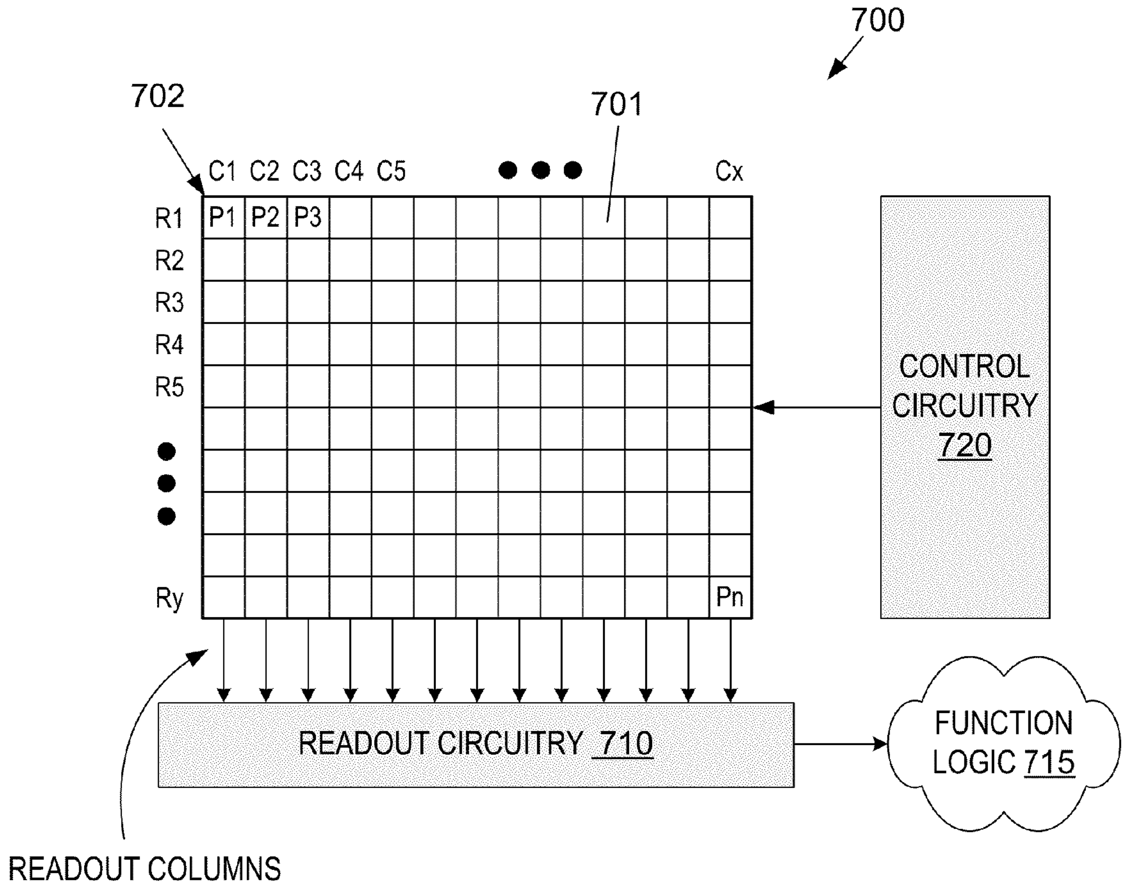
FIG. 7 is a block diagram illustrating a CMOS biosensor, in accordance with an embodiment.

FIG. 7 is a block diagram illustrating a CMOS biosensor 700, in accordance with an embodiment. The illustrated embodiment of the CMOS biosensor 700 includes pixel array 702. The pixel array 702 or the individual CMOS pixels 701 making up the pixel array 702 may have some or all of the above described characteristics. The CMOS biosensor 700 also includes at least a readout circuitry 710, a function logic 715, and a control circuitry 720. The readout circuitry 710 represents an example embodiment of a detection element to measure the background current. Pixel array 702 may be a two-dimensional array of individual CMOS pixels 701 (e.g., pixels P1, P2 . . . , Pn). As illustrated, each individual pixel 701 is arranged into a row (e.g., rows R1 to Ry) and a column (e.g., column C1 to Cx) to acquire data of an affinity based binding between an analyte and a bio-probe. These data can then be used to render a two-dimensional data set of analyte information. For example, each individual pixel may be used to detect a particular DNA sequence. An array of different pixels may allow a simultaneous detection of various DNA sequences that make up an entire genome, which is an ensemble of these various DNA sequences. In short, the CMOS biosensor 700 permits the determination of DNA sequence information of an entire genome in one measurement.

After each pixel 701 has acquired its data, the data is readout by the readout circuitry 710 and transferred to the function logic 715. By way of example, the readout circuitry 710 may include at least an amplification circuitry, an analog-to-digital conversion circuitry, or otherwise. The function logic 715 may simply store the data or even manipulate the data by applying post measurement effects. In one embodiment, readout circuitry 710 may readout a row of data at a time along readout column lines (illustrated) or may readout the data using a variety of other techniques (not illustrated), such as a column/row readout, a serial readout, or a full parallel readout of all pixels simultaneously. Control circuitry 720 is connected with the pixel array 702 to control operational characteristic of some or all of the pixels 701 that make up the pixel array 702. For example, control circuitry 720 may generate a signal or signals to alter the background current in some or all of the pixels 701 so as to improve the detection sensitivity of a particular affinity based binding bio-assay.

Figure 8:
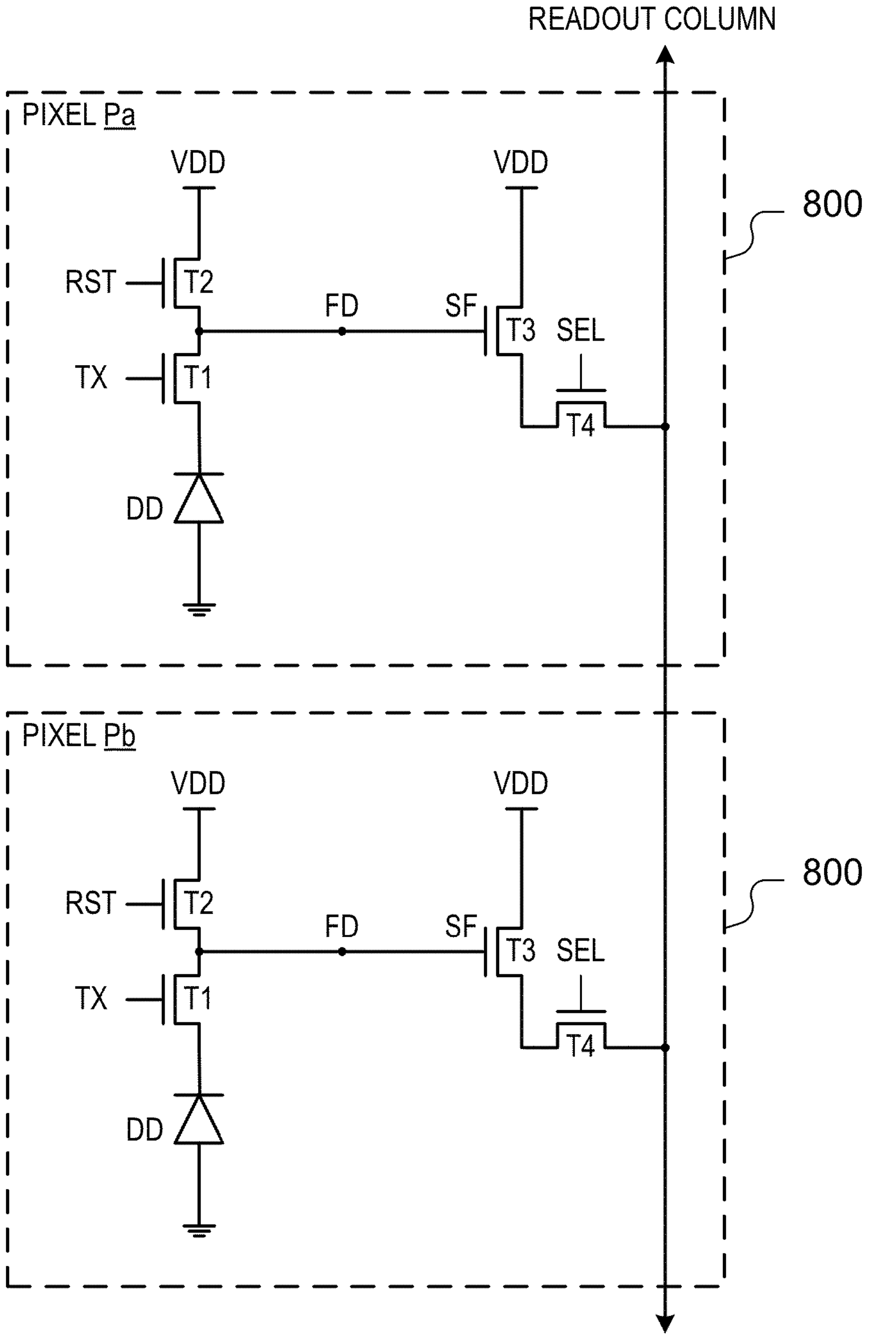
FIG. 8 is a circuit diagram illustrating sample pixel circuitry of two CMOS biosensor pixels within a biosensor array, in accordance with an embodiment.

FIG. 8 is a circuit diagram illustrating a pixel circuitry 800 of two four-transistor pixels within a pixel array, in accordance with an embodiment of the disclosure. Pixel circuitry 800 is one possible pixel circuitry architecture for implementing each pixel within pixel array 702 of FIG. 7. However, it should be appreciated that embodiments are not limited to four-transistor pixel architectures; rather, one of ordinary skill in the art having the benefit of the instant disclosure will understand that the present teachings are also applicable to three-transistor designs, five-transistor designs, and various other pixel architectures.

In FIG. 8, pixels Pa and Pb are arranged in two rows and one column. The illustrated embodiment of each pixel circuitry 800 includes a diode DD, a transfer transistor T1, a reset transistor T2, a source-follower ("SF") transistor T3, and a select transistor T4. During operation, affinity based binding between analytes and bio-probes may modulate the level of a background current in pixels Pa and Pb. Further, diode DD may have an interface with its surrounding substrate, wherein the interface may be a primary source of the background current. Transfer transistor T1 receives a transfer signal TX, which transfers the background current from the vicinity region of diode DD to a floating diffusion node FD. In one embodiment, floating diffusion node FD may be coupled to a storage capacitor for temporarily storing charges from the background current.

Reset transistor T2 is coupled between a power rail VDD and the floating diffusion node FD to reset the pixel (e.g., discharge or charge the FD and the DD to a preset voltage) under control of a reset signal RST. The floating diffusion node FD is coupled to control the gate of SF transistor T3. SF transistor T3 is coupled between the power rail VDD and select transistor T4. SF transistor T3 operates as a source-follower providing a high impedance connection to the floating diffusion FD. Finally, select transistor T4 selectively couples the output of pixel circuitry 800 to the readout column line under control of a select signal SEL.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

In the above description and in the claims, the term “coupled” may mean that two or more elements are in direct physical or electrical contact. However, “coupled” may instead mean that two or more elements are not in direct contact with each other, but yet still co-operate or interact with each other, such as, for example, through one or more intervening components or structures.

In the description above, for the purposes of explanation, numerous specific details have been set forth in order to provide a thorough understanding of the embodiments of the invention. It will be apparent however, to one skilled in the art, that other embodiments may be practiced without some of these specific details. The particular embodiments described are not provided to limit the invention but to illustrate it. The scope of the invention is not to be determined by the specific examples provided above but only by the claims below. In other instances, well-known circuits, structures, devices, and operations have been shown in block diagram form or without detail in order to avoid obscuring the understanding of the description.

Reference throughout this specification to “one embodiment”, “an embodiment”, or “one or more embodiments”, for example, means that a particular feature may be included in the practice of the invention. Similarly, in the description various features are sometimes grouped together in a single embodiment, figure, or description thereof, for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

The invention claimed is:

1. A CMOS (Complementary Metal Oxide Semiconductor) pixel for sensing at least one stimulus selected from a biological, chemical, ionic, electrical, mechanical and magnetic stimulus, comprising:

a substrate including a backside; a source coupled with the substrate to generate a background current; a first diode, and a detection system electrically coupled with the substrate to measure an effect of the background current;

at least one charge sensitive layer having an electrical charge and that is coupled with the backside, wherein the at least one charge sensitive layer is operable to interact with an analyte that is exposed to the backside, and wherein the interaction of the electrical charge layer with the analyte provides a non-light emitting stimulus that alters the electrical charge of the at least one charge sensitive layer and affects a measurable change in an effect of the background current.

2. The CMOS pixel of claim 1, wherein the detection system includes at least one selected from a diode, a transfer transistor, a reset transistor, a floating diffusion node, a source follower transistor, and a select transistor.

3. The CMOS pixel of claim 2, wherein the transfer transistor and the reset transistor act to reset the first diode to a voltage level that is in part determined by the effect of the stimulus on the background current.

4. The CMOS pixel of claim 2, wherein the transfer transistor, floating diffusion, and source follower transistor read out a voltage level from the first diode that is in part determined by the effect of the stimulus on the background current.

5. The CMOS pixel of claim 1, wherein at least one charge sensitive layer is substantially coupled with the backside.

6. The CMOS pixel of claim 1, wherein at least one charge sensitive layer is an insulating layer.

7. The CMOS pixel of claim 1, wherein at least one charge sensitive layer is within the substrate and of the same material as the substrate and adjacent to the backside of the substrate.

8. The CMOS pixel of claim 5, wherein the charge sensitive layer has a capacity of affinity based modification of the charge held within the first diode and wherein the affinity based modification of the charge held within the first diode affects a measurable change in an effect of the background current.

9. The CMOS pixel of claim 1, wherein the source to generate the background current includes a second diode that is substantially disposed within the substrate.

10. The CMOS pixel of claim 1, wherein the source to generate the background current includes a shallow trench isolation structure that is substantially disposed within the substrate, and wherein at least one of: (1) the shallow trench isolation structure includes at least one rough surface; and (2) the substrate includes a portion adjacent to the shallow trench isolation structure that includes embedded dopant atoms.

11. The CMOS pixel of claim 10, wherein the embedded dopant atoms include boron ions.

12. A sensor comprising:

a substrate having a frontside and a backside opposite the frontside, the frontside having a metal stack over Complementary Metal Oxide Semiconductor (CMOS) circuitry;

at least one of a diode and a structure, disposed within the substrate, and operable to generate a background current;

a circuit electrically coupled with the substrate and operable to measure the background current; and probes coupled with the backside and having an electrical charge, the probes operable to bind analyte, wherein the binding of the probes to the analyte is to alter the electrical charge of the probes, without a need for light emission, and is to cause a change in the background current that is sufficient to be measured by the circuit.

13. The sensor of claim 12, wherein said at least one of the diode and the structure comprises a diode, and wherein the diode has either more angles than a cuboid or fewer angles than a cuboid.

14. The sensor of claim 12, wherein said at least one of the diode and the structure comprises a shallow trench isolation (STI) structure, and wherein the STI structure has at least one rough surface, wherein the rough surface is rougher than surfaces of STI structures in CMOS image sensors.

15. The sensor of claim 12, wherein said at least one of the diode and the structure comprises a shallow trench isolation (STI) structure, and wherein the substrate includes a portion adjacent to the STI structure that includes dopant atoms at a different concentration than in a region farther away from the STI structure.

16. The sensor of claim 15, wherein the dopant atoms include boron ions.

17. The sensor of claim 12, further including at least one cantilever, wherein the probes are coupled with a surface of the at least one cantilever.

18. The sensor of claim 17, wherein the at least one cantilever is coupled with the backside through an intermediary member.

19. The sensor of claim 12, wherein the circuit is part of a pixel, and wherein the pixel is not operable to detect light.

20. The sensor of claim 19, further comprising at least one of a blocking layer and a blocking material to block the light from the pixel.

21. The sensor of claim 12, wherein said at least one of the diode and the structure comprises a photodiode that is operable to generate the background current but that is not operable to detect light.

22. The sensor of claim 21, further comprising at least one of a blocking layer and a blocking material to block the light from the photodiode.

23. A CMOS (Complementary Metal Oxide Semiconductor) pixel for sensing at least one selected from a biological, chemical, ionic, electrical, mechanical and magnetic stimulus, comprising:

a substrate including a backside;

a source coupled with the substrate to generate a background current;

a detection element electrically coupled with the substrate to measure the background current;

at least one receptor entity having an electrical charge and that is coupled with the backside, wherein the at least one receptor entity is operable to bind to an analyte that is to be exposed to the backside, and wherein the binding of the at least one receptor entity to the analyte is to alter the electrical charge of the at least one receptor entity and is to affect a measurable change in the background current, at least one of a blocking layer and a blocking material to block light from the pixel such that the pixel is not operable to detect the light.

24. A CMOS (Complementary Metal Oxide Semiconductor) pixel for sensing at least one selected from a biological, chemical, ionic, electrical, mechanical and magnetic stimulus, comprising:

a substrate including a backside;

a source coupled with the substrate to generate a background current;

a detection element electrically coupled with the substrate to measure the background current;

at least one receptor entity having an electrical charge and that is coupled with the backside, wherein the at least one receptor entity is operable to bind to an analyte that is to be exposed to the backside, and wherein the binding of the at least one receptor entity to the analyte is to alter the electrical charge of the at least one receptor entity and is to affect a measurable change in the background current, wherein the source comprises a photodiode, and wherein the photodiode is not operable to detect light such that the pixel is not operable to detect the light.

25. The CMOS pixel of claim 24, further comprising at least one of a blocking layer and a blocking material to block the light from the photodiode.

* * * * *